(12) United States Patent
Flodin

(10) Patent No.: US 6,941,945 B2
(45) Date of Patent: Sep. 13, 2005

(54) DEVICE FOR COLLECTING LIQUID FROM EXHALATION GAS FROM A PATIENT

(76) Inventor: Bjorn Flodin, Tallåsvågen 8-10, Spånga (SE), 163 43

( * ) Notice: Subject to any disclaimer, the term of this patent is extended or adjusted under 35 U.S.C. 154(b) by 252 days.

(21) Appl. No.: 10/203,251

(22) PCT Filed: Feb. 26, 2001

(86) PCT No.: PCT/SE01/00417

§ 371 (c)(1),
(2), (4) Date: Aug. 7, 2002

(87) PCT Pub. No.: WO01/62313

PCT Pub. Date: Aug. 30, 2001

(65) Prior Publication Data

US 2003/0010342 A1 Jan. 16, 2003

(30) Foreign Application Priority Data

Feb. 25, 2000 (SE) .............................. 0000635

(51) Int. Cl.[7] .............................. A62B 18/08
(52) U.S. Cl. ................. 128/201.13; 128/203.26; 128/204.17; 128/207.15
(58) Field of Search ............ 128/201.13, 201.12, 128/203.12, 203.26, 204.17, 204.18, 200.24, 201.25, 911, 206.22, 207.14–207.18; 604/19, 317, 318, 403, 405; 165/58, 59, 64, 66, 110, 177, 180, 181

(56) References Cited

U.S. PATENT DOCUMENTS 3,895,675 A * 7/1975 Rein et al. ................. 165/164
3,945,378 A * 3/1976 Paluch ................... 128/201.13
4,007,737 A * 2/1977 Paluch ................... 128/201.13
4,224,939 A   9/1980 Lang
4,318,398 A * 3/1982 Oetjen et al. ........... 128/201.13
5,452,714 A   9/1995 Anderson et al.
5,826,575 A   10/1998 Lall
6,557,551 B2 * 5/2003 Nitta ..................... 128/203.17

FOREIGN PATENT DOCUMENTS

| EP | 055997 | * 11/1992 | ............ 128/204.18 |
| GB | 1235542 | 6/1971 | |
| WO | 96/17641 | 6/1996 | |
| WO | 00/13730 | 3/2000 | |

* cited by examiner

Primary Examiner—Glenn K. Dawson
(74) Attorney, Agent, or Firm—Swidler Berlin LLP

(57) ABSTRACT

The invention refers to a device for collecting liquid from exhalation gas from a patient. The device includes a first pipe conduit (5, 8) for the supply of inhalation gas to the patient, a second pipe conduit (6, 9) for the removal of exhalation gas from the patient and a container device (1) for collecting liquid from the exhalation gas. The container device includes a first space (2), which forms a portion of the first pipe conduit (5, 8) and through which the inhalation gas thus flows, and a second space (3), which forms a portion of the second pipe conduit (6, 9) and through which the exhalation gas thus flows. The second space (3) is arranged to receive the collected liquid. The first space (2) is separated from the second space (3) by means of a wall member (4), which has a good thermal conductivity and permits transfer of heat from the exhalation gas to the inhalation gas.

25 Claims, 2 Drawing Sheets

DEVICE FOR COLLECTING LIQUID FROM EXHALATION GAS FROM A PATIENT

THE BACKGROUND OF THE INVENTION AND PRIOR ART

The present invention refers to a device for collecting liquid from exhalation gas from a patient.

The introduction of such devices for the supply of inhalation gas and the removal of exhalation gas, so called intubation, is made as a matter of routine in medical treatment of patients which need external breath support from a respirator. Such devices normally include a plastic pipe, a so called endotracheal tube, which via the throat is guided down into the trachea to a position at the dividing region of the main bronchi. The endotracheal tube is fixed in the trachea by means of a fixing member which is provided slightly above the distal end of the tube and inflated to airtight abutment against the inner wall of the trachea. Air exchange, i.e, supply of relatively oxygen-rich inhalation gas and removal of exhalation gas, takes place through one single channel in the tube, which via an external manifold is connected to the supply outlet and removal inlet, respectively, of the respirator.

The body reacts in a natural way against foreign bodies and organisms, which are present in the airways, by an increased excretion of secretion from the mucous membranes in combination with an increased activity of the cilia. The purpose of the cilia is to catch and transport impurities and secretion out of the body by moving in such a way that they transfer an upwardly directed movement to these impurities and secretion.

When the tracheal tube is installed in the trachea, the cilia may not act any longer in the intended manner since the tracheal tube and the fixing member closes the natural transport way for the secretion, i e the natural cleaning system is by-passed. In addition, the tracheal tubes, which are used today, do not have a satisfactory capability of removing the secretion since the same quantity of gas is transported successively in both directions through the channel of the tracheal tube. Due to these two factors, the secretion and phlegm will be collected in the airways beneath the fixing member. In order not to close off completely the airways by phlegm and thereby prevent an efficient gas exchange, the airways has to be sucked continuously, typically in intervals of 2–3 hours night and days, to drain collected phlegm. Such suction drainage is performed by means of a catheter, which is guided down through the tracheal tube and which, by means of a subpressure, sucks secretion to a collecting container. However, suction drainage by means of a catheter is a process which is time-consuming and expensive, and frequently involves complications. Some usual such complications are injuries on the mucus membranes, infections by contamination of the lower respiratory tract, coincident alveoli in the lungs, acute oxygen deficit, heart disorder and unprepared extubation. In addition, the patient is subjected to significant stress, discomfort and a sense of suffocation. There are also other grounds frequently involving pneumonia due to the treatment by conventional endotracheal tubes. Since the fixing member is positioned far down in the trachea in order to minimise the exposure to the secretion producing surface of the trachea, secretion containing bacteria will remain above the fixing member. During exhalation it is not unusual with leakage at the fixing member, wherein contaminated secretion is drawn downwardly into the lungs during the subsequent inhalation.

PCT/SE99/01517 discloses one solution of the problems mentioned above, and more precisely a device, which includes a pipe member intended to be introduced down into trachea of a patient. The pipe member includes a feeding pipe, which has a distal outlet opening arranged to be located at the dividing region of the main bronchi of the patient during use of the device, and a discharge pipe, which has an inlet opening arranged above said outlet opening and through which the feeding pipe extends. By such a pipe member, exhalation gas may be conveyed away from the patient and collected in a container device. The container device may be replaceable and when it is full it may be replaced by a new, empty container device.

SUMMARY OF THE INVENTION

The object of the present invention is to improve the supply of inhalation gas to the patient and to provide an effective container device, which is easy to handle, for collecting liquid from the exhalation gas.

This object is obtained by a device, which includes the features defined in claim 1.

By such a device, a device is obtained by which liquid in an efficient and elegant manner may be collected form the exhalation gas of a patient connected to a respirator. Thanks to the heating member, the inhalation gas may be given a temperature in the vicinity of the body temperature of the patient when the inhalation gas reaches the lungs of the patient. In such way, the risk of cooling down the patient is reduced. In addition, the treatment will be more gentle and comfortable to the patient. The heating member may be realised in may different manners, for instance by heat exchange with any medium, an external source in the form of for instance an electric conduit etc. It is to be noted, that the first space may have a substantially arbitrary shape according to the most general aspect of the invention. Thereby, the heating member may also be arranged to extend along substantially the whole length of the first pipe conduit.

According to an embodiment of the invention, the device includes a container device, which includes the first space and the second space. Such a container device facilitates the handling of the collected liquid.

According to a further embodiment of the invention, the first space is separated from the second space by means of a wall member, which has a good thermal conductivity and permits transfer of heat from the exhalation gas to the inhalation gas. Thereby, the heating member may be formed by the wall member and the inhalation gas may be given a temperature, which is close to the temperature of the exhalation gas. Previous problems with a too cold inhalation air may thus be avoided in a very simple manner. The preheating of the inhalation gas may be made without any external heat source, and in such a way, the device becomes independent of the function of connecting systems. The device is therefore very well suited for use in mobile systems, for instance ambulances.

According to an embodiment of the invention, said wall member includes surface increasing means. By such means, an efficient heat transfer between the first space and the second space may be obtained. Thereby, said wall member may have a folded shape. By such a folded or wave-like shape, a substantially larger wall surface is obtained and thus also an increased transfer of heat through the wall between the spaces.

According to a further embodiment of the invention, the container device includes a longitudinal axis, which extends through the first space and the second space and which is intended to extend substantially vertically when the container device is in an active state of use in such a way that the first space is located above the second space. By such a design, the heat from the warmer exhalation gas will be transferred to the inhalation gas due to the fact that the heat rises upwardly.

According to a further embodiment of the invention, a first shielding member is provided in the first space and arranged to convey the inhalation gas along a curved path through the first space. In such a way, the inhalation gas will be located in the first space during a relatively long time period and thus be able to absorb a larger quantity of heat from the exhalation gas. In same manner, at least a second shielding member may be provided in the second space and arranged to convey the exhalation gas along a path through the second space, which path includes at least one bend. Thereby, not only emission of a larger part of heat from the exhalation gas but also a more efficient separation of heat from the exhalation gas for collection in the second space is obtained.

According to a further embodiment of the invention, the device includes means, which permits the supply of humidity to the inhalation gas. In such a way, the advantage is obtained that the inhalation air to the patient may be given a humidity, which decreases the irritation of the mucous membranes during the respirator treatment. Thereby, said means may include a passage of the container device for the supply of liquid to the first space. The liquid may be supplied in a liquid state or as a mist or vapour. Furthermore, the first space may include a part space, which is arranged to house a volume of liquid for said humidifying of the inhalation gas. In such a way, it is possible to let the inhalation gas pass the volume of liquid and thus to obtain a higher humidity. The part space may partly be delimited by said wall member, which permits a heating of the liquid in the part space and in such a way more humidity may be transferred to the inhalation gas.

According to a further embodiment of the invention, a disinfectant may be provided in the second space and arranged to be distributed in the collected liquid. In such a way, the risk of contamination from the collected liquid may be reduced. Said disinfectant may advantageously be provided in a number of separate areas along a path, which extends from a lower region of the second space to an upper region of the second space, wherein said disinfectant is arranged to be released successively when the level of the collected liquid rises in the second space.

According to a further embodiment of the invention, the device includes a level indicator, which is provided in the second space and arranged to indicate the level of the collected liquid. In such a way, the persons taking care of the patient may know if the container device is full, and need to be replaced. The level indicator may be designed in different manners, for instance it may include a medium, which in contact with liquid initiates a recognisable change of the liquid.

According to a further embodiment of the invention, the second pipe conduit includes at least one pie portion, which extends into the second space and includes an orifice for the entry of the exhalation gas in the second space. Thereby, the level indicator may be formed by the pipe portion, which is designed in such a manner that an audible sound is formed during said entry when the level of the collected liquid reaches the pipe portion due to formation of bubbles. Such an audible sound may for instance be created by means at least one recess of the pipe portion, which extends from said orifice.

According to a further embodiment of the invention, the first pipe conduit and the second pipe conduit are connected to a pipe member, which is intended to be introduced into the trachea of a patient. Thereby, the first pipe conduit and the second pipe conduit between the container device and the pipe member may form an integrated conduit, in which the first pipe conduit extends within the second pipe conduit. By such a design, also a certain heat exchange from the exhalation gas to the inhalation gas is made possible downstream the first space. In such a way, a condensation of humidity in the inhalation gas may be reduced or prevented. The first pipe conduit and the second pipe conduit may extend from the container device by an external conduit arrangement, which is arranged to be connectable to a respirator. Advantageously, the integrated conduit and the external conduit arrangement are releasable connected to the container device by means of connecting members, which may have a suitable design and preferably permit a relatively simple release and attachment. In such a way replacement of the container device is facilitated.

According to a further embodiment of the invention, the pipe member includes a feeding member, which is connected to the first pipe conduit and which has a distal outlet opening that is arranged to be positioned at the dividing region of the main bronchi of the patient during use of the device, and a discharge pipe, which is connected to the second pipe conduit and which has an inlet opening that is arranged above said outlet opening. Thereby, the second pipe conduit may transport exhalation gas from the trachea to the second space of the container device. The inlet opening for the exhalation gas may thereby be provided immediately below the larynx, which permits the cilia in the trachea to operate essentially normally and thus transport secretion towards the inlet opening. The secretion, which is secreted may thus in an efficient manner be transported away by the exhalation gas without being mixed with the inhalation gas. Advantageously, the pipe member may include a fixing member, which is arranged to be introduceable into the trachea and to permit airtight fixing of the pipe member in the trachea, wherein the fixing member is arranged to be provided substantially immediately beneath the larynx of the patient and wherein the inlet opening of the discharge pipe is provided substantially immediately beneath the fixing member and at a substantial distance from the outlet opening of the feeding pipe. Furthermore, the pipe member may include a distance member, which is provided around the feeding pipe between said inlet opening and said outlet opening, and is arranged to ensure that the feeding pipe is located at a distance from at least one part of the inner wall of the trachea.

BRIEF DESCRIPTION OF THE DRAWINGS

The present invention is now to be explained more closely by means of an embodiment, which is described as an example, and with reference to the drawings attached, in which FIG. 1 discloses a sectional view of a container device of the device according to the invention, and FIG. 2 discloses a pipe member of the device according to the invention.

DETAILED DESCRIPTION OF AN EMBODIMENT OF THE INVENTION

Figure 1:
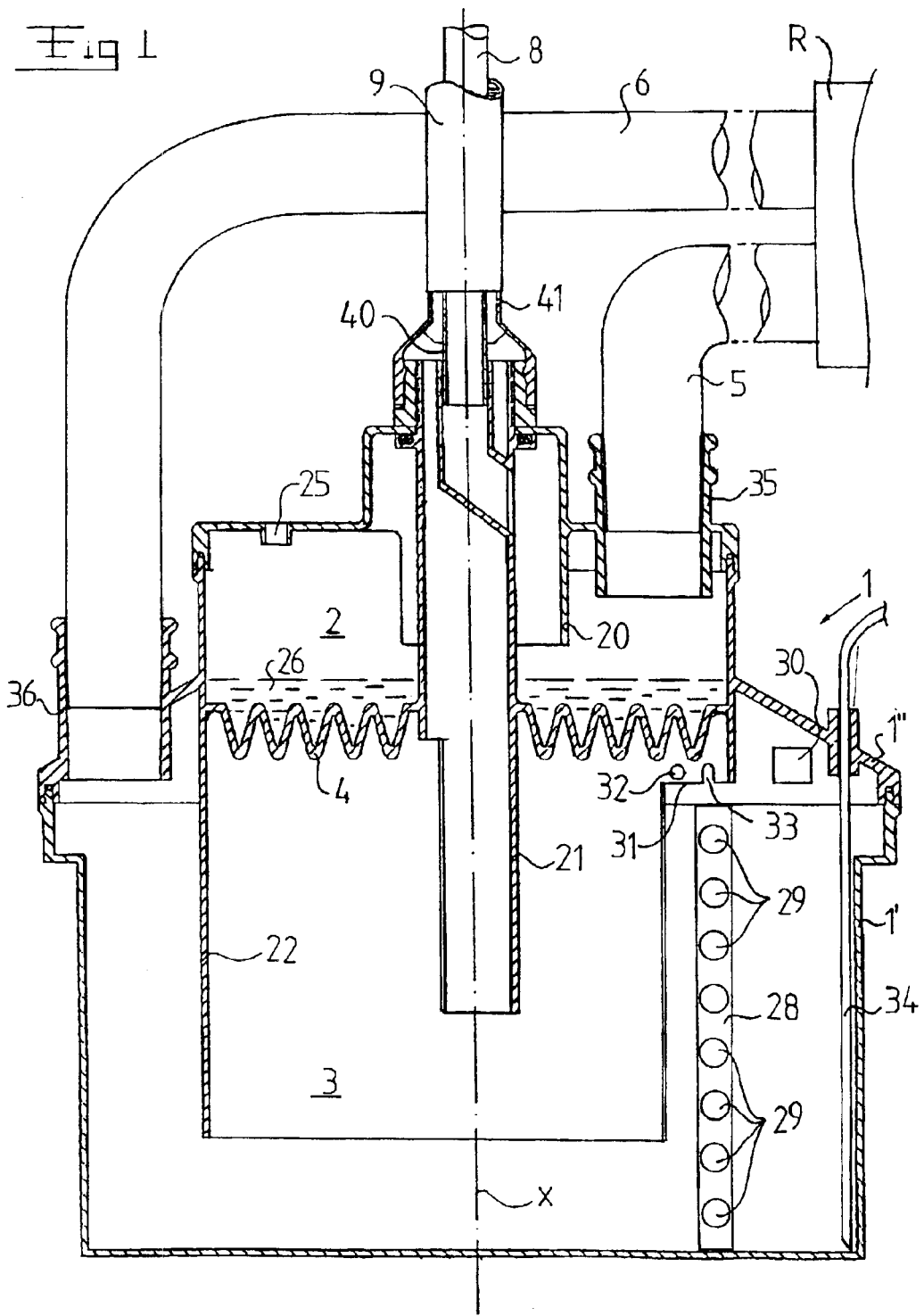

FIG. 1 discloses a container device 1, which encloses a first space 2 and a second space 3. The first space 2 is separated from the second space 3 by means of a wall member 4. The wall member 4 forms a bottom of the first space 2 and extends in a horizontal plane when the container device 1 is in an active state of use. The wall member 4 extends perpendicularly to a longitudinal axis x, which extends substantially vertically through the first space 2 and the second space 3 in said state of use.

The container device 1 is intended to be connected to a schematically indicated respirator R by means of a first external pipe conduit 5, which extends from the respirator R to the first space 2 for the supply of inhalation air to the first space 2. A container device 1 is also connected to the respirator R via a second external pipe conduit 6, which is connected to the second space 3 and arranged to permit removal of exhalation gas from the second space 3.

Figure 2:
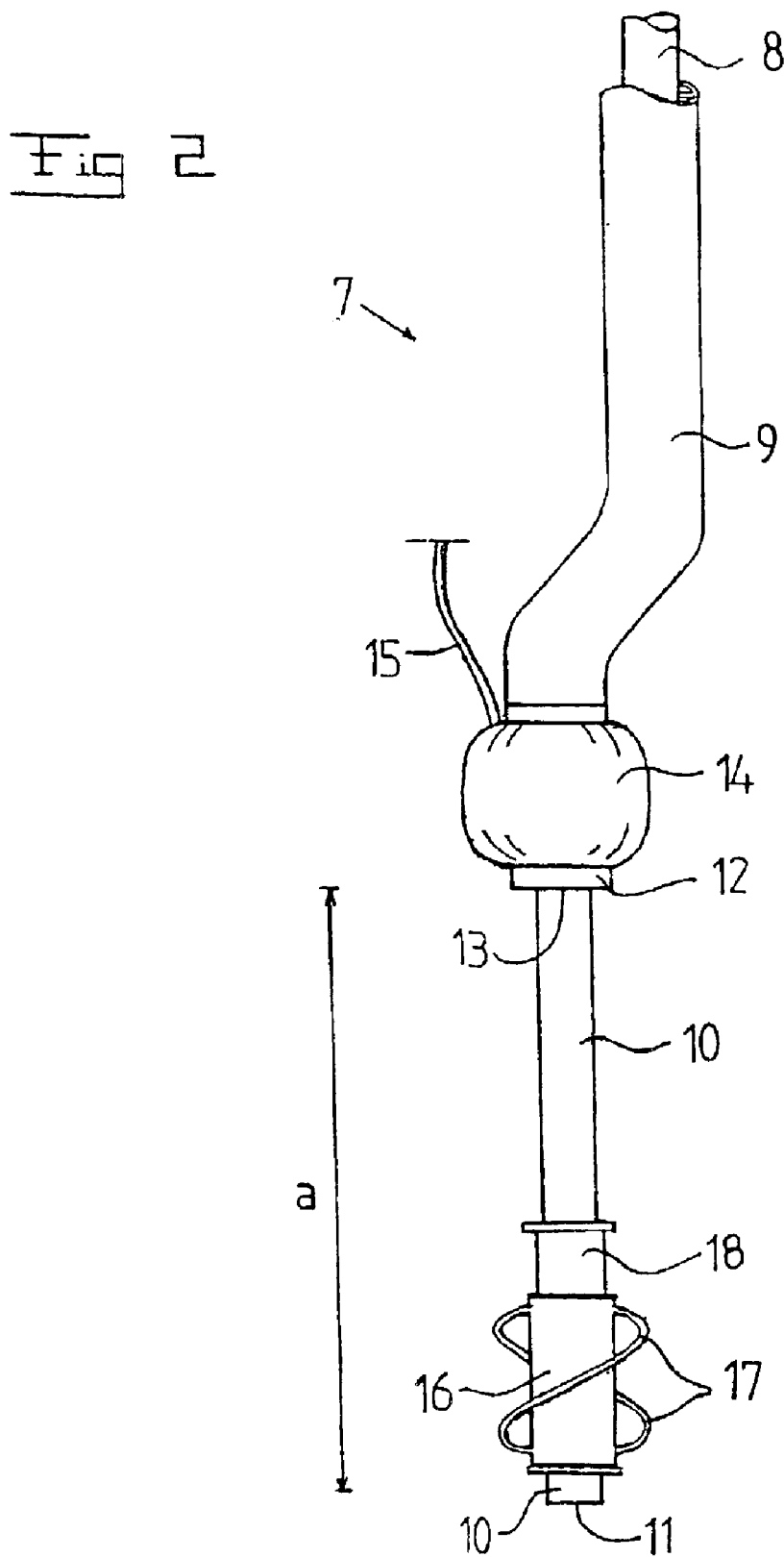

Furthermore, the container device 1 is arranged to be connected to a pipe member 7 (see FIG. 2), which is arranged to be introduced into the trachea of a patient. Thereby, a first pipe conduit 8 from the pipe member 7 extends to the first space 2 of the container device 1 for the supply of inhalation gas from the first space 2 to the pipe member 7 and the patient. Furthermore, a second pipe conduit 9 extends from the pipe member 7 to the second space 3 of the container device 1 for the supply of exhalation gas from the patient and the pipe member 7 to the second space 3.

The pipe member 7 includes a feeding pipe 10, which is connected to the first pipe conduit 8. The feeding pipe 10 has a distal outlet opening 11, which is arranged to be located at the dividing region of the main bronchi of the patient when the pipe member 7 is introduced into the trachea of the patient. Furthermore, the pipe member 7 includes a discharge pipe 12, which has an inlet opening 13 for the exhalation gas. The inlet opening 13 is provided proximally at a distance a from the distal outlet opening 11. Furthermore, the pipe member 7 includes a fixing member 14, which is arranged to permit fixing of the pipe ember 7 in the trachea substantially immediately below the larynx of the patient. The inlet opening 13 of the discharge pipe 12 is located substantially immediately below the fixing member 14. The fixing member 14 includes an expansion body, which is arranged to be expandable to sealing abutment against the inner wall of the trachea by the supply of a medium via a conduit 15. Furthermore, the pipe member 7 includes a distance member 16, which is provided around the feeding pipe 10 between the inlet opening 13 and the outlet opening 11 and arranged to ensure that the feeding member 10 is located at a distance from the inner wall of the trachea. The distance member 16 includes two recilient or elastic elements 17, which are arranged to abut the inner wall of the trachea. The elements 17, which may be more than two have a cord-like shape and extends in a helical path with regard to a centre axis through the feeding pipe 10. In order to facilitate the introduction and removal of the pipe member 7 into and out of the trachea, the distance member 16 may be rotateable relative to the feeding member 10. Furthermore, the distance member 16 may be provided on a base element 18, which is fixedly attached to the feeding member 10. The distance member 16 may advantageously be permitted to move axially on the base element 18 in order to prevent injuries on the mucous membrane in the trachea.

The container device 1 includes a first shielding member 20, which is provided in the first space 2 and arranged to convey the inhalation gas, which is supplied via the first external conduit 5 in a path with at least one bend, through the first space 2 before the inhalation gas exits through the first pipe conduit 8. In such a way, the inhalation gas will be given a certain retention time in the first space 2.

The second pipe conduit 9 is connected to a pipe portion 21, which extends through the first space 2 and into the second space 3. This pipe portion 21 forms a second shielding member, which is provided in the second space 3 and arranged to convey the exhalation gas from the second pipe conduit 9 in a path, which includes at least one bend, through the second space 3 before it may exit through the second external pipe conduit 6. As appears from FIG. 1, the container device 1 includes a further second shielding member 22, which also is designed as a pipe portion and arranged to convey the exhalation gas in a path through the second space 3, which path includes at least one bend. By means of these two shielding members 21 and 22, the exhalation gas is thus conveyed in a path, which in the embodiment disclosed includes two significant bends and which significantly prolongs the route of the exhalation gas through the second space in relation to the shortest distance between the pipe portion 21 and the second external pipe conduit 6. The second shielding member 21 is, as appears from FIG. 1, provided substantially concentrically within the further second shielding member 22. Thanks to the long flow route of the exhalation gas through the second space 3, the liquid which is present in the exhalation gas will be separated from the gas and collected in a lower part of the second space 3.

The wall member 4 between the two spaces 2 and 3 is manufactured of a material with a good thermal conductivity. Such a good thermal conductivity may be obtained by a plastic material or a metallic material. The wall member 4 is thus to permit transfer of heat from the exhalation gas to the inhalation gas. An effective transfer of heat is also obtained if the wall member 4 includes surface increasing means. In the embodiment disclosed, the wall member 4 has been given a surface increasing, folded shape. Thereby, the total heat transfer through the wall member 4 is increased. Also other types of surface increasing means may be utilised. For instance, the wall member 4 may be provided with flanges, which project into the first space 2 and/or into the second space 3. Thanks to the fact that the first space 2 is located above the second space 3, heat from the exhalation gas will move upwardly through the wall member 4 to the first space 2.

Furthermore, the container device 1 includes means in the form of a passage 25, which enable the supply of humidity to the inhalation gas which is located in the first space 2. Thereby, humidity in the form of a mist or steam may be introduced into the first space 2 through the passage 25 by means of suitable supply members (not disclosed). However, it is also possible to supply liquid through the passage 25, wherein the liquid will be collected in a part space in a lower part of the first space 2 in such a way that a volume 26 of liquid is formed in this part space. This liquid volume 26 will emit humidity, which may be absorbed by the inhalation gas flowing through the first space 2. The part space is partly delimited by the wall member 4 and thus the liquid volume 26 will be heated by the exhalation gas, which permits a more efficient emission of humidity from the liquid volume 26 to the inhalation gas.

It is also to be noted that the passage 25 permits the supply of medicaments to the inhalation gas.

Advantageously, the container device 1 includes a disinfectant 28, which is provided in the second space 3 and arranged to be distributed successively in the collected liquid. The disinfectant 28 is provided on an inner wall of the second space 3. In the embodiment disclosed, the disinfectant is provided in a number of separate areas 29, which are arranged along a path or on a strip extending from a lower region of the second space 3 to an upper region of the second space 3. In such a way, the disinfectant will be released successively when the level of the collected liquid rises in the second space 3. Consequently, the growth of microorganisms in the collected liquid may be prevented or at least reduced. It is to be noted, that the disinfectant 28 may be distributed in many different manners in the second space 3. For instance, the disinfectant may be applied as a powder on the bottom of the second space 3. Thereby, it is important that so much disinfectant is applied that the disinfecting effect is maintained until the second space 3 is filled with the collected liquid. It is also possible to apply the disinfectant 28 only in one area 29. The disinfectant may also be applied by spraying or surface treatment of the inner wall and/or the bottom wall of the second space 3.

Furthermore, the container device 1 includes a level indicator 30, which is provided in the second space 3 and arranged to indicate when the collected liquid has reached a certain level in the second space 3. The level indicator 30 includes a medium, which in contact with the collected liquid initiates a recognisable change of the liquid. One such medium may for instance include a substance activating a chemical and/or biological reaction, for instance a precipitation, a colour change, a bubble formation etc. The medium may also include a colouring matter, which is solubly bounded in any substance and which is released from this substance when the liquid comes into contact with the substance and the colouring matter. In such a way, the liquid in the second space 3 will be coloured by the colouring matter when the liquid reaches the level at which the level indicator 30 and thus the colouring matter is located. The container device 1 includes a further level indicator, which is formed by the sound which is generated when the liquid reaches an upper part of the further second shielding member 2. At this upper part there is a substantially horizontal edge 31, which at lease partly defines an orifice of the pipe portion or the shielding member 2, and when the exhalation gas passes this edge when the liquid level is at the level of the edge 31, an audible sound will be formed. This sound generating effect may be amplified by means of the hole 32 or the recess 31, which extends upwardly from the edge 31.

When the container device 1 is full, it may be replaced by a new empty container device 1, wherein the pipe conduits 5, 6, 8, 9, are released from the full container device 1 and are connected to the new one. It is also possible to empty the full container device 1 by means of a suction conduit 34, which extends down into the second space 3 and is connected to a vacuum source (not disclosed). A further possibility would be release a lower part 1' of the container device 1 from an upper part 1" thereof.

The external pipe conduits 5 and 6 are connectable to the container device 1 by means of pipe studs 35 and 36, respectively, which enclose a respective pipe conduit 5, 6. The pipe studs 35, 36 may include locking devices (not disclosed) for attaching the pipe conduits 5, 6. The pipe conduits 8, 9 are connected to the container device 1 by the fact that the pipe studs 41, 45 are introduceable into the pipe conduits 8 and 9, respectively. Preferably, the connecting members or pipe studs 35, 36, 40 and 41 are designed to permit a relatively quick attachment and release of the pipe conduits 5, 6, 8, 9.

The present invention is not limited to the embodiment disclosed but may be varied and modified within the scope of the following claims.

The first pipe conduit 8, does not need to extend coaxially in the second pipe conduit 9, as is disclosed in the embodiment described, but these two pipe conduits 8, 9 may be designed as two parallel separate pipe conduits having the same external dimension. The pipe member 7 may also be designed in many different manners.

The two spaces 2 and 3 do not need to be provided in one and same container device but may be formed by separate containers. Thereby, it is also to be noted that an external heating member, for instance an electric conduit, may be utilised for heating the inhalation gas in the first space.

It is also possible, within the scope of the invention, to provide an external heating member in the first space 2, as is disclosed in FIG. 1, in addition to the heat transferring wall member 4.

The device may also include a temperature sensor, which is arranged to sense the temperature of the inhalation gas. By means of the sensed temperature, the temperature of the inhalation gas may be adjusted to a more suitable value. This can be done in a simple manner by means of an electric conduit as a heating member. Also by the container device disclosed, the temperature control may be obtained by for instance a rotation of one or several of the shielding members 20, 21, 22.

What is claimed is:

1. A device for collecting liquid from exhalation gas from a patient, including a first pipe conduit for the supply of inhalation gas to the patient, a second pipe conduit-for the removal of exhalation gas from the patient, a first space, which forms a portion of the first pipe conduit and through which the inhalation gas thus flows, and a second space, which forms a portion of the second pipe conduit and through which the exhalation gas thus flows, wherein the second space is arranged to collect said liquid and wherein the first space is separated from the second space by a wall member and includes a heating member arranged to heat the inhalation gas and wherein the wall member has adequate thermal conductivity to permit transfer of heat from the exhalation gas to the inhalation gas and which thus forms said heating member.

2. A device according to claim 1, including a container device, which includes the first space and the second space.

3. A device according to claim 2, wherein said wall member includes surface increasing means.

4. A device according to claim 3, wherein said wall member has a folded shape.

5. A device according to claim 2, wherein the container device includes a longitudinal axis, which extends through the first space and the second space and which is intended to extend substantially vertically when the container device is in an active state of use in such a way that the first space is located above the second space.

6. A device according to claim 2, including means, for permitting the supply of humidity to the inhalation gas.

7. A device according to claim 6, wherein said means includes a passage of the container device for the supply of liquid to the first space.

8. A device according to claim 7, wherein the first space includes a part space, which is arranged to house a volume of a liquid for said humidifying of the inhalation gas.

9. A device according to claim 8, wherein the part space partly is delimited by said wall member.

10. A device according to claim 2, where the first pipe conduit and the second pipe conduit are connected to a pipe member, which is intended to be introduced into the trachea of a patient.

11. A device according to claim 10, wherein the first pipe conduit and the second pipe conduit between the container device and the pipe member form an integrated conduit, in which the first pipe conduit extends within the second pipe conduit.

12. A device according to claim 11, wherein the first pipe conduit and the second pipe conduit extend from the container device by an external conduit arrangement, which is arranged to be connectable to a respirator.

13. A device according to claim 12, wherein the integrated conduit and the external conduit arrangement are releasably connected to the container device by means of connecting members.

14. A device according to claim 11, wherein the pipe member includes a feeding member, which is connected to the first pipe conduit and which has a distal outlet opening that is arranged to be positioned at the dividing region of the main bronchi of the patient during use of the device, and a discharge pipe, which is connected to the second pipe conduit and which has an inlet opening that is arranged above the said outlet opening.

15. A device according to claim 14, wherein the pipe member includes a fixing member, which is arranged to be introducible into the trachea and to permit airtight fixing of the pipe member in the trachea, wherein the fixing member is arranged to be provided substantially immediately beneath the larynx of the patient and wherein the inlet opening of the discharge pipe is provided substantially immediately beneath the fixing member and at a substantial distance from the outlet opening of the feeding member.

16. A device according to claim 14, wherein the pipe member includes a distance member, which is provided around the feeding member between said inlet opening and said outlet opening, and is arranged to ensure that the feeding member is located at a distance from at least one part of an inner wall of the trachea.

17. A device according to claim 1, wherein a first shielding member is provided in the first space and arranged to convey the inhalation gas along a path through the first space, which path includes at least one bend.

18. A device according to claim 17, wherein a second shielding member is provided in the second space and arranged to convey the exhalation gas along a path through the second space, which path includes at least one bend.

19. A device according to claim 1, wherein a disinfectant is provided in the second space and arranged to be distributed in the collected liquid.

20. A device according to claim 19, wherein said disinfectant is provided in a number of separate areas along a path, which extends from a lower region of the second space to an upper region of the second space, and wherein said disinfectant is arranged to be released successively when the level of the collected liquid rises in the second space.

21. A device according to claim 1, wherein the level indicator which is provided in the second space and arranged to indicate the level of collected liquid.

22. A device according to claim 21, wherein the level indicator includes a medium, which in contact with the liquid initiate a recognizable change of the liquid.

23. A device according to claim 21, wherein the second pipe conduit includes at least one pipe portion, which extends into the second space and includes an orifice for the entry of the exhalation gas into the second space.

24. A device according to claim 23, wherein the level indicator is formed by a pipe portion, which is designed in such a manner that an audible sound is formed during said entry when the level of the collected liquid reaches the pipe portion.

25. A device according to claim 24, wherein the pipe portion includes at least one recess, which extends from said orifice.

* * * * *

UNITED STATES PATENT AND TRADEMARK OFFICE
CERTIFICATE OF CORRECTION

PATENT NO. : 6,941,945 B2
DATED : September 13, 2005
INVENTOR(S) : Björn Flodin

It is certified that error appears in the above-identified patent and that said Letters Patent is hereby corrected as shown below:

Column 10,
Lines 15-16, should read:
-- A device according to claim 1, including a level indicator, which is provided in the second space and arranged to indicate the level of collected liquid. --.
Line 20, "initiate" should read -- initiates. --.

Signed and Sealed this

Twentieth Day of December, 2005

JON W. DUDAS
*Director of the United States Patent and Trademark Office*